(12) United States Patent
Alonso Fernandez et al.

(10) Patent No.: US 6,649,192 B2
(45) Date of Patent: Nov. 18, 2003

(54) APPLICATION OF NANOPARTICLES BASED ON HYDROPHILIC POLYMERS AS PHARMACEUTICAL FORMS

(75) Inventors: Maria Jose Alonso Fernandez, La Coruna (ES); Pilar Calvo Salve, La Coruna (ES); Carmen Remunan Lopez, La Coruna (ES); Jose Luis Vila Jato, La Coruna (ES)

(73) Assignee: Universidade de Santiago de Compostela (ES)

( * ) Notice: Subject to any disclaimer, the term of this patent is extended or adjusted under 35 U.S.C. 154(b) by 0 days.

(21) Appl. No.: 09/908,372

(22) Filed: Jul. 18, 2001

(65) Prior Publication Data

US 2001/0051189 A1 Dec. 13, 2001

Related U.S. Application Data

(63) Continuation of application No. 09/043,979, filed as application No. PCT/ES96/00186 on Oct. 22, 1996, now abandoned.

(30) Foreign Application Priority Data

Jul. 29, 1996 (ES) .............................. 9601685

(51) Int. Cl.[7] .......................... A61K 9/16; A61K 47/36
(52) U.S. Cl. ....................... 424/499; 424/501
(58) Field of Search ............... 424/499, 501, 424/409; 514/951–52; 530/817

(56) References Cited

U.S. PATENT DOCUMENTS 5,346,703 A 9/1994 Viegas et al. ............... 424/486
5,840,341 A * 11/1998 Watts et al.

FOREIGN PATENT DOCUMENTS

| WO | WO 9605810 | 2/1996 |
| WO | WO20698 | * 7/1996 |

* cited by examiner

Primary Examiner—Edward J. Webman
(74) Attorney, Agent, or Firm—Ostrolenk, Faber, Gerb & Soffen, LLP

(57) ABSTRACT

Application of nanoparticles based on hydrophilic polymers as pharmaceutical forms for the administration of active macromolecules. The nanoparticles (having a nanometric size and a hydrophilic character), also called nanospheres or latex, are colloidal systems comprised of the combination of hydrophilic polymers and an active ingredient having a high molecular weight (active macromolecule, molecular weight higher than 1000 daltons). The hydrophilic polymers are the chitosan (an aminopolysaccharide) or its derivatives and polyoxyethylene or its derivatives. The association of the active macromolecule to said nanoparticles takes place in an aqueous phase without having to use organic solvents or auxiliary toxic substances. The active ingredient charge capacity of the nanoparticles is extremely high and additionally said charge is released in a controlled and time extended way. Additionally, said nanoparticles have a positive surface electric charge whose intensity may vary in relation to its composition.

20 Claims, 2 Drawing Sheets

APPLICATION OF NANOPARTICLES BASED ON HYDROPHILIC POLYMERS AS PHARMACEUTICAL FORMS

This is a continuation of U.S. patent application Ser. No. 09/043,979, filed May 22, 1998, now abandoned, which is a 371 of PCT/ES96/00186, filed Oct. 22, 1996.

DESCRIPTION

Application of nanoparticles based on hydrophilic polymers as pharmaceutical forms for the administration of bioactive molecules.

The major constituents of these nanoparticles are two hydrophilic polymers: chitosan, which has a positive charge, and poly(oxyethylene), which has a non-ionic character. The active ingredient, which may be also a major constituent of these nanoparticles, is an antigenic or therapeutic macromolecule (peptide, protein, oligonucleotide, RNA, DNA . . . ). The electrical charge of these colloidal particles can vary, depending on the ratio of the two hydrophilic polymers, from a highly positive value to a near zero value. The size of the nanoparticles can be modulated as well, from few nanometers to a few microns, by adequately selecting the preparation conditions.

Chitosan is a natural cationic polymer produced by deacetylation of the polysaccharide chitin which is obtained from crustacean shells. Chitosan is available in the market in a variety of forms (with different molecular weights and degrees of deacetylation and, also, in the form of chitosan base or chitosan salt: e.g., hydrochlorhydrate, glutamate, lactate).

Poly(oxyethylene) or poly(ethylene oxide) (PEO) is a synthetic non-ionic polymer. PEO and its block copolymers with poly(propylene oxide) (PPO) are available in the market with different molecular weights and various ratios of ethylene oxide to propylene oxide groups. These block copolymers, especially the one containing 80% ethylene oxide, have been extensively used in the preparation of parenteral colloidal drug carriers because of their lack of toxicity.

Bioactive macromolecules can be associated with these nanoparticles by different extents depending on the composition of the nanoparticles (on the ratio of the two main hydrophilic polymers and on the physicochemical characteristics of the macromolecule which is associated).

The incorporation of bioactive macromolecules within the nanoparticles can be achieved by a very simple and mild procedure which is particularly effective for preserving the stability of the macromolecules.

The formation of the nanoparticles occurs spontaneously due to the simultaneous precipitation of chitosan and the bioactive macromolecule caused by the incorporation of a molecule with a basic character, i.e., sodium tripolyphosphate (counter anion). This process can be also considered as a process of ionic gelation or ionic crosslinking of chitosan with the counter anion. In this method, the utilization of organic solvents, extreme pH conditions or auxiliary substances of toxic nature are avoided.

The association of bioactive macromolecules with the nanoparticles occurs by a combined mechanism which may involve ionic and non-ionic interactions between the bioactive macromolecule and chitosan and a physical entrapment process. The ionic interaction between chitosan and negatively charged polymers has been previously described as the main mechanism involved in the formation of microcapsules by complex coacervation (T. Takahashi, K. Takayama, Y. Machida and N. Nagai, Chitosan-Alginate complex coacervate capsules: effects of calcium chloride, plasticizers and polyelectrolites on mechanical stability, Biotechnology Progress, 4, 76–81, 1988) and of polyion complexes (M. M. Daly and D. Knoor. Characteristics of polyion complexes of chitosan with sodium alginate and sodium polyacrylate, Int. J. Pharm. 61, 35–41, 1990). However, the association of bioactive macromolecules to nanoparticles made of chitosan or chitosan-PEO, according to an ionic interaction mechanism, has not yet been described. In addition, the originality here relies in the fact that the incorporation of the bioactive macromolecule into the nanoparticles occurs upon the incorporation of an ionic crosslinking agent such as sodium tripolyphosphate.

The current interest of hydrophilic nanoparticles is clearly illustrated by the growing amount of literature in this field. In this respect, it is worthwhile to mention several papers describing various methods of preparation of nanoparticles made of natural hydrophilic polymers and macromolecules (W. Lin, A. G. A. Coombes, M. C. Garnett, M. C. Davies, E. Stacht, S. S. Davis and L. Illum., Preparation of sterically stabilized human serum albumin nanospheres using a novel dextrano-MPEG crosslinking agent, Pharm. Res., 11, 1588–1592, 1994). (H. J. Watzke and C. Dieschbourg, Novel silica-biopolymer nanocomposites: the silica sol-gel process in biopolymer organogels, Adv. Colloid. Interface Sci. 50, 1–14, 1994), (M. Rajaonarivony, C. Vauthier, G. Courrage, F. Puisiex and P. Couvreur, Development of a new drug carrier from alginate, J. Pharm. Sci., 82, 912–917, 1993). However, the application of these nanoparticles for the association and delivery of high molecular weight active compounds such as peptides, proteins, antigens and oligonucleotides has not been described thus far. This could be partially due to the fact that most of the procedures described until now for the preparation of nanoparticles involve the use of organic solvents and/or covalent crosslinking agents as well as drastic conditions such as high temperatures or emulsification processes, which are extremely harmful for bioactive macromolecules. On the other hand, it has recently also been proposed the use of amphiphilic synthetic nanoparticles made of copolymers of lactic acid and PEO, for the delivery of macromolecules (P. Quellec, R. Gref, P. Calvo, M. J. Alonso and E. Dellacherie, Encapsulation of a model protein and a hydrophobic drug into long-circulating biodegradable nanospheres, Proceed. Intern. Symp. Control. Rel. Bioact. Mater., 23, 815–816 1996). Once again, however, the main limitation of these nanoparticles is the necessity of using organic solvents and emulsification processes for their preparation.

Despite the important efforts which have been dedicated over the last years to the formulation of macromolecules, nothing has been reported so far dealing with the application of chitosan or chitosan-PEO nanoparticles for the association and delivery of bioactive macromolecules with therapeutic or immunological interest. The preparation of chitosan nanoparticles without using harmful crosslinking agents such as aldehydes has not been yet reported either.

The new pharmaceutical composition described in this patent, based on the association of bioactive macromolecules to hydrophilic nanoparticles, overcomes problems previously encountered in the formulation of macromolecules. As indicated before, the main ingredients of the nanoparticles are two hydrophilic polymers: chitosan or chitosan salts and PEO or the block copolymers of poly(oxyethylene)-poly(oxypropylene) (PEO-PPO). The presence of PEO or PEO-PPO is not a requisite for the formation of the nanoparticles; however, the incorporation of these polymers in the system makes it more versatile since they affect the physicochemical properties of the nanoparticles such as the particles's size and zeta potential, as well as their release behavior and increase their biocompatibility. The chitosan: PEO ratio can vary enormously, reaching a value of 1:50. The association efficiency of the bioactive macromolecules to the nanoparticles can reach values as high as 100%.

The nanoparticles covered in this invention, which are intended for the association and delivery of bioactive macromolecules, offer numerous advantages over other types of nanoparticles previously described in the literature. These advantages rely not only in their preparation conditions but also from the point of view of their application for the administration of macromolecules by various routes. The most important benefits include: (1) the procedure for the incorporation of the bioactive macromolecule to the nanoparticles is instantaneous and does not require the use of ingredients which could be toxic for humans such as organic solvents, oils and aldehydic crosslinking agents; (2) the physicochemical properties of the nanoparticles, more specifically, their size, hydrophilic surface and surface charge, can be modulated by simply adjusting the ratio of CS and PEO; (3) these nanoparticles have an extraordinary capacity for the association of active ingredients of high molecular weight (macromolecules) and (4) they can deliver the associated active ingredient at different rates.

With respect to the routes by which these new nanoparticles can be administered to the human organism, it is convenient to distinguish between those which involve the contact of the nanoparticles with an epithelial or mucosal surface such as the buccal, oral, topical, transdermal, nasal, pulmonar, ocular and vaginal routes, and the parenteral routes which involve the injection of the coloidal particles. In the first case (epithelial, mucosal routes), the contact of the particles with the epithelium or the mucosa which are negatively charged can be favored by providing the nanoparticles with a high positive surface charge. In the second case (parenteral routes), especially following intravenous administration, these nanoparticles offer the possibility of modulating the biodistribution of the active molecules associated with them.

The nanoparticles covered in this invention are presented as colloidal suspensions in an external aqueous medium in which other ingredients i.e., cryprotective preservatives, viscosizers, salts . . . , could eventually be incorporated.

In the context of the present invention, the active ingredient (synonymous with a bioactive macromolecule) is the ingredient for which the formulation is designed and, therefore, the ingredient that will have a particular effect following its administration to an organism. The effect could be to prevent, palliate or treat a disease and also to improve the physical appearance (delivery of cosmetic agents).

The pharmaceutical systems described here are characterized in that they have a size smaller than 1 $\mu$m (nanoparticles) and a great capacity for the association of bioactive macromolecules. The size of the nanoparticles is mainly dependent on the chitosan concentration in the nanoparticles formation medium. Thus, for a very low chitosan aqueous concentration (lower than 0.01%) or a very high chitosan aqueous concentration (higher than 0.5%), an aqueous gel solution or a suspension of microparticles (larger than 1 $\mu$m) is formed respectively. In addition, the size of the particles can be also modulated by incorporating PEO or PEO-PPO in the nanoparticles formation medium.

As an example, results presented in Table 1 show the important augmentation in the nanoparticle size (from 275 nm to 685 nm) caused by the incorporation of increasing amounts of PEO-PPE in the medium (the chitosan/PEO-PPO ratio varied from 1/0 up to 1/50). Results in Table 1 also show that the incorporation of PEO-PPO to the nanoparticles led to a significant reduction in their zeta potential values.

The great capacity of the nanoparticles for the association of bioactive macromolecules has been demonstrated for several proteins (bovine serum albumin, insulin, tetanus toxoid, diphtheria toxoid) and oligonucleotides. Using bovine serum albumin (BSA) as a model therapeutic protein, it was shown that its association efficiency (percent of macromolecule incorporated with respect to the amount of macromolecule to be incorporated) to the nanoparticles was very high and influenced by the BSA concentration and the presence of PEO-PPO in the nanoparticles formation medium (Table 2). The size and zeta potential of the nanoparticles were not affected by the incorporation of BSA into the nanoparticles. On the other hand, it was observed that the stage at which the BSA was incorporated into the process has a remarkable effect on its association efficiency to the nanoparticles. Results in Table 3 reveal that a maximum association efficiency was achieved when the BSA was dissolved in the sodium tripolyphosphate aqueous solution and then added to the chitosan aqueous solution. In contrast, a minimum incorporation efficiency was obtained when the BSA was incorporated after the sodium tripolyphosphate, in other words, once the nanoparticles were formed. Finally, it was also observed that the pH of the nanoparticles formation medium has an important role in the incorporation efficiency of the protein into the nanoparticles. Results in table 4 indicate that the higher the pH, the more important was the percentage of BSA incorporated into the nanoparticles. Results of the incorporation of tetanus and diphtheria toxoids into chitosan nanoparticles are presented in Table 5. These data provide evidence that the toxoids can be efficiently incorporated into the chitosan nanoparticles.

Another interesting feature of the chitosan nanoparticles described here is that they can deliver the macromolecule incorporated into them for extended periods of time. Furthermore, it was found that it is possible to modulate the release of the active ingredient from the nanoparticles by adjusting its loading and also by the presence of PEO-PPO in the nanoparticles.

Figure 1:
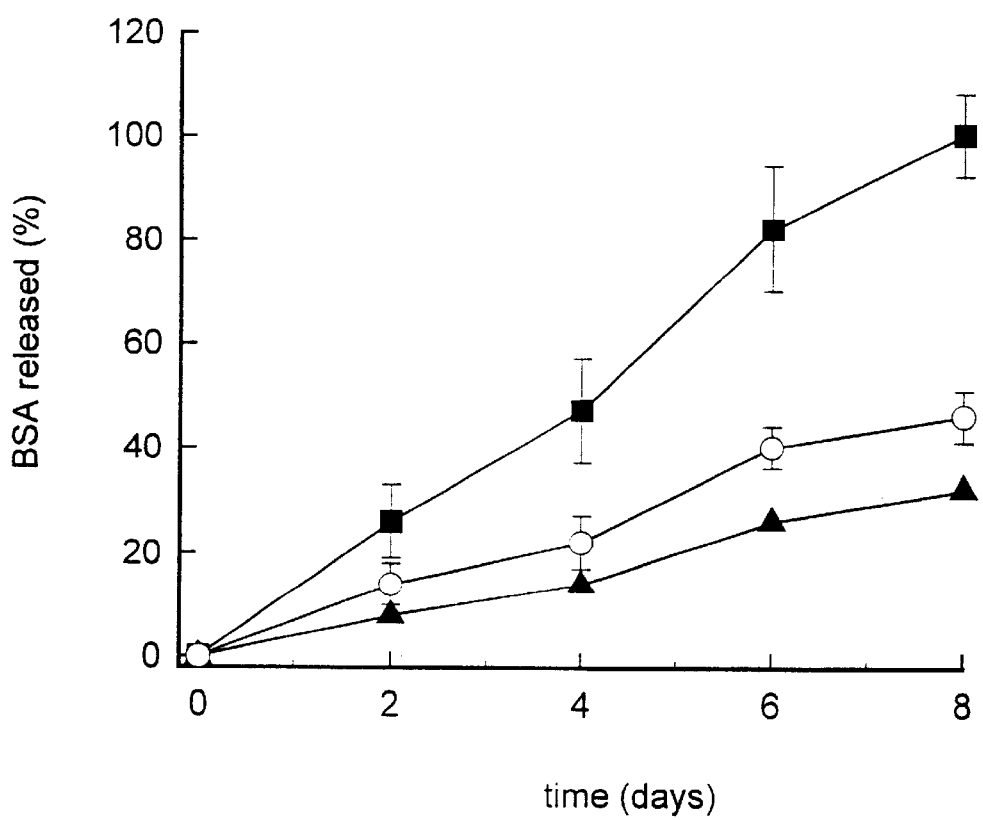
FIG. 1 displays the percentages of BSA released "in vitro" from nanoparticles made of different chitosan/PEO-PPO ratios, 1/0 (▲), 1/5 (Φ) and 1/25 (○), following their incubation at 37° C. for different time periods.
Figure 2:
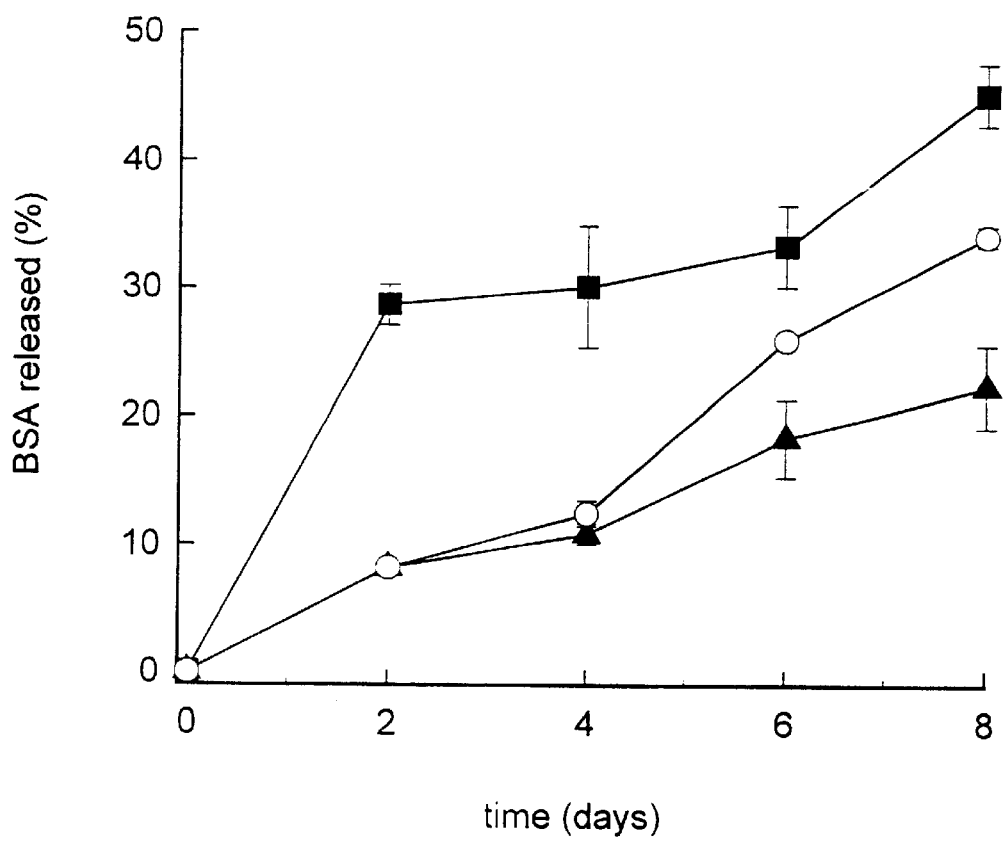
FIG. 2 displays the percentages of BSA released "in vitro" from nanoparticles containing different BSA loadings (amount of BSA entrapped in 100 mg of nanoparticles), 41% (○), 25% (Φ) and 20% (▲), following their incubation at 37° C. for different time periods.

Results depicted in FIG. 1 indicate that the presence of PEO-PPO in the nanoparticles significantly increases the BSA in vitro release rate. Results showed in FIG. 2 indicate that the higher the loading, the faster the release rate is.

In summary, this invention covers a new pharmaceutical composition which can be used for the delivery of bioactive macromolecules following their administration by different routes: topic, oral, nasal, pulmonary, vaginal, ocular, subcutaneous, intramuscular and intravenous.

Some examples of the composition and preparation of various formulations of nanoparticles are described below.

EXAMPLE 1

Association of BSA (bovine serum albumin) to chitosan nanoparticles. The composition of the formulation (nanoparticles suspension) in % (w/w) was as follows:

| | |
|---|---|
| Chitosan base | 0.14% |
| Sodium tripolyphosphate | 0.02% |
| BSA | 0.014% |
| Water | up to 100% |

Chitosan was dissolved at the concentration of 0.2% (w/v) in 25 ml of 0.05M acetic acid solution. The pH of the solution was adjusted to pH 5.0. Then, 5 mg of BSA was dissolved in the chitosan solution. Finally, 10 ml of a sodium tripolyphosphate aqueous solution (0.1%, w/v) were added to the chitosan aqueous solution containing the BSA and the system was maintained under magnetic stirring for 30 min, after the spontaneous formation of the nanoparticles.

The size, zeta potential and BSA association efficiency for this formulation were: 402 nm, 46 mV and 100% respectively.

EXAMPLE 2

Association of BSA (bovine serum albumin) to chitosan/PEO-PPO (1/5) nanoparticles. The composition of the formulation in % (w/w) was as follows:

| | |
|---|---|
| Chitosan base | 0.14% |
| PEO-PPO | 0.70% |
| Sodium tripolyphosphate | 0.02% |
| BSA | 0.014% |
| Water | upto 100% |

Nanoparticles were prepared as described in example 1 with the exception that PEO-PPO was dissolved in the chitosan solution prior to the incorporation of BSA and the pH of the chitosan solution was adjusted to pH 4.0.

The size, zeta potential and BSA association efficiency for this formulation were: 519 nm, 44 mV and 78.2% respectively.

EXAMPLE 3

Association of BSA (bovine serum albumin) to chitosan/PEO-PPO (1/25) nanoparticles. The composition of the formulation in % (w/w) was as follows:

| | |
|---|---|
| Chitosan base | 0.14% |
| PEO-PPO | 3.50% |
| Sodium tripolyphosphate | 0.02% |
| BSA | 0.014% |
| Water | up to 100% |

Nanoparticles were prepared as described in example 1 with the exception that PEO-PPO was dissolved at the concentration indicated above in the chitosan solution prior to the incorporation of BSA and the pH of the chitosan solution was adjusted to pH 4.

The size, zeta potential and BSA association efficiency for this formulation were: 741 nM, 34 mV and 45.9%, respectively.

EXAMPLE 4

Association of tetanus toxoid to chitosan nanoparticles. The composition of the formulation in % (w/w) was as follows:

| | |
|---|---|
| Chitosan base | 0.14% |
| Tetanus toxoid | 0.014% |
| Sodium tripolyphosphate | 0.02% |
| Water | up to 100% |

Nanoparticles were prepared as described in example 1 except for adding tetanus toxoid instead of BSA to the chitosan solution at the concentration indicated above.

The size, zeta potential and tetanus toxoid association efficiency for this formulation were: 245 nm, 35 mV and 53%, respectively.

EXAMPLE 5

Association of diphtheria toxoid to chitosan nanoparticles. The composition of the formulation in % (w/w) was as follows:

| | |
|---|---|
| Chitosan base | 0.14% |
| Diphtheria toxoid | 0.007% |
| Sodium tripolyphosphate | 0.02% |
| Water | up to 100% |

Nanoparticles were prepared as described in example 1 but adding diphtheria toxoid instead of BSA to the chitosan solution at the concentration indicated above.

The size, the zeta potential and the tetanus toxoid association efficiency for this formulation were: 245 nm, 36 mV and 55%, respectively.

TABLE 1

Mean values of particle size and zeta potential of nanoparticles composed of different chitosan/PEO-PPO ratios.

| Chitosan/PEO-PPO (w/w) | Size* (nm) | Zeta potential# (mV) |
|---|---|---|
| 1/0 | 275 ± 17 | 44 ± 1 |
| 1/2.5 | 283 ± 11 | 41 ± 2 |
| 1/5 | 300 ± 14 | 40 ± 1 |
| 1/25 | 430 ± 20 | 28 ± 1 |
| 1/50 | 685 ± 27 | 18 ± 1 |

*Determined by Photon Correlation Spectroscopy
Determined by Laser Doppler Anemometry

TABLE 2

Particle size. zeta potential and association efficiency of chitosan nanoparticles containing different chitosan/BSA ratios.

| Chitosan/BSA Association (w/w) | Size * (nm) | Zeta potential# (mV) | efficiency (%) |
|---|---|---|---|
| 10/1 | 402 ± 24 | 45 ± 1 | 80 ± 3 |
| 4/1 | 359 ± 35 | 45 ± 1 | 43 ± 3 |
| 2/1 | 375 ± 26 | 45 ± 1 | 26 ± 1 |
| 1/1 | 368 ± 72 | 46 ± 2 | 21 ± 2 |

* Determined by Photon Correlation Spectroscopy
Determined by Laser Doppler Anemometry

TABLE 3

Association efficiency of bovine serum albumin (BSA) to chitosan nanoparticles as a function of the stage at which BSA was incorporated and the theoretical chitosan/BSA ratio.

| | | | |
|---|---|---|---|
| Chitosan/BSA (w/w) | BSA association efficiency (%) | | |
| BSA + nanoparticles | BSA + chitosan | BSA + TPP | |
| 10/1 | | 80.4 ± 3.2 | 100 ± 1.2 |
| 2/1 | 10.8 ± 3 | 26.8 ± 0.7 | 45.2 ± 3.9 |
| 1/1 | | 21.6 ± 2.0 | 41.8 ± 2.0 |

TABLE 4

Association efficiency of bovine serum albumin (BSA) to chitosan nanoparticles as a function of the pH of the chitosan solution and the theoretical chitosan/BSA ratio.

| | | | |
|---|---|---|---|
| Chitosan/BSA (w/w) | BSA association efficiency (%) | | |
| pH 3 | pH 4 | pH 5 | |
| 10/1 | 66.8 ± 7.2 | 80.4 ± 3.2 | 91.7 ± 3.6 |
| 2/1 | 25.7 ± 1.4 | 26.8 ± 0.7 | 39.1 ± 2.4 |
| 1/1 | 19.4 ± 3.6 | 21.6 ± 2.0 | 35.5 ± 5.1 |

TABLE 5

Association efficiency of tetanus and diphtheria toxoids to chitosan nanoparticles.

| Toxoid | Chitosan/Toxoid | % Association |
|---|---|---|
| Tetanus | 1/0.06 | 56.7 ± 2.7 |
| Diphtheria | 1/0.12 | 53.3 ± 4.2 |
| Diphtheria | 1/0.12 | 55.1 ± 5.5 |

What is claimed is:

1. A pharmaceutical composition for the administration of a bioactive macromolecule comprising hydrophilic nanoparticles consisting essentially of chitosan or a derivative thereof, and optionally a poly(oxyethylene) derivative, ionically cross-linked with a triphosphate salt, and including the bioactive macromolecule, wherein said composition was prepared in the absence of an organic solvent.

2. A pharmaceutical composition according to claim 1 wherein the nanoparticles have a positive electrical charge.

3. A pharmaceutical composition according to claim 1 wherein said phosphate salt is selected from the group consisting of monophosphates, diphosphates, polyphosphates, and a derivative thereof.

4. A pharmaceutical composition according to claim 1 wherein said poly(oxyethylene) derivative is present and is selected from the group consisting of poly(oxyethylene) and block copolymers of ethylene oxide and propylene oxide.

5. A pharmaceutical composition according to claim 4 wherein the nanoparticles have a positive electrical charge.

6. A pharmaceutical composition according to claim 5 wherein said phosphate salt is selected from the group consisting of monophosphates, diphosphates, polyphosphates, and a derivative thereof; said poly (oxyethylene) derivative is selected from the group consisting of poly(oxyethylene) and block copolymers of ethylene oxide and propylene oxide; and wherein said bioactive macromolecule is selected from the group consisting of peptides, proteins, polysaccharides and polynucleotides, having a therapeutic or antogenic activity.

7. A pharmaceutical composition according to claim 6, wherein said poly(oxyethylene) derivative is present in a percentage, with respect to the total weight of the composition, of up to 60% (w/w) and said bioactive macromolecule is present in a percentage, with respect to the total weight of the composition, of up to 60% (w/w).

8. A pharmaceutical composition according to claim 7 in a form appropriate for parenteral administration or by mucosal routes wherein the nanoparticles have an electrical charge from +0.5 mV to +50 mV.

9. A pharmaceutical composition according to claim 8, wherein said bioactive macromolecule is tetanus toxoid.

10. A pharmaceutical composition according to claim 8, wherein said bioactive macromolecule is diptheria toxoid.

11. A pharmaceutical composition according to claim 1 wherein said bioactive macromolecule is selected from the group consisting of peptides, proteins, polysaccharides and polynucleotides, having a therapeutic or antogenic activity.

12. A pharmaceutical composition according to claim 11, wherein said bioactive macromolecule is tetanus toxoid.

13. A pharmaceutical composition according to claim 11, wherein said bioactive macromolecule is diptheria toxoid.

14. A pharmaceutical composition according to claim 1, wherein said poly(oxyethylene) derivative is present in a percentage, with respect to the total weight of the composition, of between 0% and 60% (w/w).

15. A pharmaceutical composition according to claim 1, wherein said bioactive macromolecule is present in a percentage, with respect to the total weight of the composition, of between 0% and 60% (w/w).

16. A pharmaceutical composition according to claim 1 including an absorption enhancer.

17. A pharmaceutical composition according to claim 1 in a form appropriate for parenteral administration or by mucosal routes wherein the nanoparticles have an electrical charge from +0.5 mV to +50 mV.

18. A pharmaceutical composition according to claim 1 wherein the nanoparticles are spontaneously formed in aqueous medium by ionic cross-linking and subsequent precipitation.

19. A pharmaceutical composition according to claim 7 for topical administration wherein the nanoparticles have an electrical charge from +0.5 mV to +50 mV.

20. A pharmaceutical composition for the administration of a bioactive macromolecule comprising hydrophilic nanoparticles consisting of chitosan or a derivative thereof, and optionally a poly(oxyethylene) derivative, ionically cross-linked with a hydrosoluble phosphate salt, and including the bioactive macromolecule, said nanoparticles having a positive electrical charge, wherein said poly(oxyethylene) derivative is present in a percentage, with respect to the total weight of the composition, of up to 60% (w/w) and said bioactive macromolecule is present in a percentage, with respect to the total weight of the composition, of up to 60% (w/w); and wherein said composition was prepared in the absence of an organic solvent.

* * * * *